US012648791B2

(12) United States Patent      (10) Patent No.:    US 12,648,791 B2

Xia et al.                (45) Date of Patent:      Jun. 9, 2026

(54) CIRCUMCISION EQUIPMENT

(71) Applicant: Wuhu ShangRing Technology Co., Ltd, Wuhu (CN)

(72) Inventors: Shujie Xia, Shanghai (CN); Huarong Yu, Beijing (CN); Jingjing Shang, Wuhu (CN); Jianzhong Shang, Wuhu (CN)

(73) Assignee: Wuhu ShangRing Technology Co., Ltd., Wuhu (CN)

( * ) Notice: Subject to any disclaimer, the term of this patent is extended or adjusted under 35 U.S.C. 154(b) by 101 days.

(21) Appl. No.: 18/625,234

(22) Filed: Apr. 3, 2024

(65) Prior Publication Data

US 2024/0245431 A1     Jul. 25, 2024

Related U.S. Application Data

(60) Division of application No. 16/531,139, filed on Aug. 5, 2019, now Pat. No. 11,980,390, which is a
(Continued)

(30) Foreign Application Priority Data

| Feb. 4, 2017 | (CN) | ......................... | 201710063339.X |
| Feb. 4, 2017 | (CN) | ......................... | 201710063340.2 |
| Feb. 4, 2017 | (CN) | ......................... | 201710065136.4 |
| Feb. 4, 2017 | (CN) | ......................... | 201710065137.9 |
| Feb. 4, 2017 | (CN) | ......................... | 201710065138.3 |
| Feb. 4, 2017 | (CN) | ......................... | 201710065139.8 |
| Feb. 4, 2017 | (CN) | ......................... | 201710065140.0 |
| Feb. 4, 2017 | (CN) | ......................... | 201710065146.8 |
| Feb. 4, 2017 | (CN) | ......................... | 201710065147.2 |
| Feb. 4, 2017 | (CN) | ......................... | 201710065148.7 |
| Feb. 4, 2017 | (CN) | ......................... | 201710065149.1 |
| Feb. 4, 2017 | (CN) | ......................... | 201710065150.4 |
| Feb. 4, 2017 | (CN) | ......................... | 201720109034.3 |
| Apr. 18, 2017 | (CN) | ......................... | 201710250780.9 |
| Apr. 18, 2017 | (CN) | ......................... | 201710250951.8 |
| Apr. 19, 2017 | (CN) | ......................... | 201710254989.2 |
| Apr. 19, 2017 | (CN) | ......................... | 201710255021.1 |
| Apr. 19, 2017 | (CN) | ......................... | 201710255023.0 |

(Continued)

(51) Int. Cl.
     *A61B 17/326*      (2006.01)
     *A61B 17/068*      (2006.01)
(Continued)

(52) U.S. Cl.
     CPC ........ *A61B 17/326* (2013.01); *A61B 17/0682* (2013.01); *A61B 17/072* (2013.01);
(Continued)

(58) Field of Classification Search
     CPC .............. A61B 17/326; A61B 17/0682; A61B 17/1155
     See application file for complete search history.

(56) References Cited

FOREIGN PATENT DOCUMENTS

| CN | 204890072 | * 12/2015 |
| CN | 106214224 | * 12/2016 |

* cited by examiner

*Primary Examiner* — Thomas Mcevoy
(74) *Attorney, Agent, or Firm* — JEEN IP LAW, LLC

(57) ABSTRACT

The present invention relates to surgical devices, particularly to a circumcision apparatus, enable the circumcision apparatus to be suitable for different surgery objects and environments.

10 Claims, 6 Drawing Sheets

Related U.S. Application Data continuation of application No. PCT/CN2018/074988, filed on Feb. 1, 2018.

(30)        Foreign Application Priority Data

| | | |
|---|---|---|
| Apr. 19, 2017 | (CN) | .......................... 201710255025.X |
| Apr. 24, 2017 | (CN) | .......................... 201710273894.5 |
| Apr. 24, 2017 | (CN) | .......................... 201710273895.X |
| Apr. 24, 2017 | (CN) | .......................... 201710274306.X |
| Apr. 24, 2017 | (CN) | .......................... 201710274307.4 |
| Apr. 24, 2017 | (CN) | .......................... 201710274308.9 |
| Apr. 24, 2017 | (CN) | .......................... 201710274309.3 |
| Apr. 24, 2017 | (CN) | .......................... 201710274396.2 |
| Apr. 24, 2017 | (CN) | .......................... 201710274397.7 |
| Apr. 24, 2017 | (CN) | .......................... 201710274398.1 |
| Apr. 24, 2017 | (CN) | .......................... 201710274399.6 |
| Apr. 24, 2017 | (CN) | .......................... 201710274400.5 |
| Apr. 24, 2017 | (CN) | .......................... 201710274426.X |
| Aug. 18, 2017 | (CN) | .......................... 201710709597.0 |

(51)   Int. Cl.

| | |
|---|---|
| *A61B 17/072* | (2006.01) |
| *A61B 17/115* | (2006.01) |
| *A61B 90/00* | (2016.01) |
| *A61B 17/00* | (2006.01) |

(52)   U.S. Cl.

CPC .......... *A61B 17/1155* (2013.01); *A61B 90/08* (2016.02); *A61B 2017/00561* (2013.01); *A61B 2017/07228* (2013.01); *A61B 2017/07285* (2013.01); *A61B 2090/0811* (2016.02)

15-1

4-3

CIRCUMCISION EQUIPMENT

CROSS REFERENCE TO RELATED APPLICATIONS

The present application is a Divisional Application of U.S. patent application Ser. No. 16/531,139 filed on Aug. 5, 2019, which is a Continuation Application of PCT Application No. PCT/CN2018/074988 filed on Feb. 1, 2018, which claims the benefit of Chinese Patent Application Nos. 201710063339.X, 201710065146.8, 201710065140.0, 201710065139.8, 201710065138.3, 201710065150.4, 201710065149.1, 201710065148.7, 201710065147.2, 201710063340.2, 201710065137.9, 201710065136.4, 201720109034.3 filed on Feb. 4, 2017, Chinese Patent Application Nos. 201710250780.9 and 201710250951.8 filed on Apr. 18, 2017, Chinese Patent Application Nos. 201710254989.2, 201710255021.1, 201710255023.0 and 201710255025.X filed on Apr. 19, 2017, Chinese Patent Application Nos. 201710274426.X, 201710274400.5, 201710274399.6, 201710274398.1, 201710274397.7, 201710274396.2, 201710274309.3, 201710274308.9, 201710274307.4, 201710274306.X, 201710273895.X and 201710273894.5 filed on Apr. 24, 2017, and Chinese Patent Application No. 201710709597.0 filed on Aug. 18, 2017. All the above are hereby incorporated by reference.

FIELD OF THE INVENTION

The present invention relates to surgical devices, particularly to a circumcision apparatus and more particularly to a C-type valgus circumcision stapler.

BACKGROUND OF THE INVENTION

Refer to the C-type valgus circumcision stapler. The redundant prepuce or phimosis is one of the causes of male urinary system infections and sexually transmitted diseases. The redundant prepuce or phimosis can cause urinary tract infections, resulting in chronic prostatitis, with a series of symptoms, such as pains in back and waist, impotence and premature ejaculation. Therefore, the removal of the redundant prepuce is a good way to prevent these diseases.

Traditionally, surgical removal of the phimosis or redundant prepuce has the main technical points of removal of excess prepuce, hemostasis, and apposition suture of cut edges to skin. A postoperative patient cannot move around, suffers unbearable pain in each change of ointment and endures huge pain when stitches are taken out finally. In addition, incomplete ligating hemostasis will cause prepuce hematoma, thus requiring a surgical treatment again. Furthermore, since the prepuce removal and the hemostasis processes are performed separately, the surgery time is prolonged, and the patient's panic is exacerbated.

A therapeutic method of applying a laser and high-frequency electric surgical knife technology to circumcision has been developed at present. Although this therapeutic method substitutes for scissors cutting and makes a bleeding spot coagulated, the patient's tissues will be burnt and susceptible to infection.

Then, a circumcision device was developed in this field. In the circumcision device, a prepuce incision is sutured using a suturing nail in one step. However, during a surgery using a conventional built-in circumcision stapler in the prior art, a front prepuce and most of a penis are exposed outside, so that the prepuce and the penis are vulnerable to injury or infection. A portion above a prepuce clamping portion of the built-in circumcision stapler is located outside the circumcision stapler, while a U-nail suturing position is located at the top of the circumcision stapler. Once hemorrhage caused by instrument failure or misoperation occurs, a patient is likely to be infected to cause a surgical accident. The built-in circumcision stapler has a built-in circumcision knife, and thus carries out cutting inside and nailing at periphery. In case of a redundant prepuce or the like, the possibility of cutting of overlapped tissues is high, causing pain and risks. In addition, if circumcision and hemostasis with U-nails are performed as soon as appropriate clamping is realized only through cooperation between an upper cover (upper comprehensive cover) and a lower cover (lower comprehensive cover/connecting cover) as well as between an inner ring (prepuce fixing hoop) and an inner comprehensive cover (U-nail top ring and/or thimble guide block), a prepuce blood vessel cannot be accurately positioned as a built-in nail groove is not visible. As a result, the U-nail in the U-nail groove cannot accurately correspond to the prepuce blood vessel during the surgery, so that a hemostasis effect is poor. Even, the head of the U-nail may be just hammered into the blood vessels, resulting in a surgery risk as hemostasis is not punctual. Moreover, in the existing technology, as the U-nail is directly hammered into the prepuce, the U-nail is likely to adhere with the prepuce and even U-nail cannot peel off punctually as the U-nail deeply penetrates into the prepuce in a process of waiting for necrosis and defluvium of the prepuce and peeling off of the U-nail after the surgery, causing severe pain to the patient.

SUMMARY OF THE INVENTION

Refer to the C-type valgus circumcision stapler.

In view of the above technical problems in the prior art, an object of the present invention is to provide a valgus circumcision stapler. Through the structure of the valgus circumcision stapler, most of a front prepuce is accommodated in the circumcision stapler, and a clamping portion and a circumcision portion of the valgus circumcision stapler are both built-in, so that hemorrhage infection and the like are avoided. An external circumcision knife and a blood vessel docking device reduce a risk in a surgery, and a provided U-pin gasket avoids the failure of the peeling off of a U-nail later. The specific technical solutions are as follows.

A C-type valgus circumcision stapler comprises: an upper comprehensive cover, a lower comprehensive cover, a prepuce fixing hoop and a U-nail device, wherein the upper comprehensive cover and the lower comprehensive cover are releasably connected in a matching manner;

a part or all of the prepuce fixing hoop is placed in the upper comprehensive cover;

a part or all of the U-nail device is placed in the lower comprehensive cover; and the prepuce fixing hoop is capable of being positioned in the upper comprehensive cover and cooperates with the upper comprehensive cover to clamp a prepuce, and/or the lower end of the prepuce fixing hoop is capable of cooperating with the U-nail device to clamp the prepuce.

Further, the U-nail device comprises a U-nail top ring and a thimble guide block; the thimble guide block is configured to accommodate a suturing U-nail and/or to guide the movement of the suturing U-nail and/or to position and/or guide a thimble of the U-nail top ring; and the U-nail top ring is configured to cooperate with the thimble guide block to eject the U-nail in the thimble guide block.

Further, the C-type valgus circumcision stapler further comprises a U-nail gasket.

Further, the U-nail gasket further comprises a gasket positioning stage perpendicular to and/or at an angle to the plane of the U-nail gasket; and the gasket positioning stage is one or more protrusions and/or an integral annular protrusion arranged at the inner circumference and/or the outer circumference and/or the middle of the plane of the U-nail gasket.

Further, a first through hole is formed in the middle of the thimble guide block; the thimble guide block comprises an annular inner wall and/or an annular outer wall and/or a positioning stage accommodating groove; the annular inner wall is configured to cooperate with the one or more protrusions and/or integral annular protrusion arranged at the inner circumference of the plane of the U-nail gasket for positioning; and/or, the annular outer wall is configured to cooperate with the one or more protrusions and/or integral annular protrusion arranged at the outer circumference of the plane of the U-nail gasket for positioning; and/or, the positioning stage accommodating groove is formed at the top end of the thimble guide block, and is configured to accommodate the one or more protrusions and/or integral annular protrusion at the middle of the plane of the U-nail gasket.

Further, the thimble guide block is provided with a plurality of thimble guide grooves annularly formed in the annular thimble guide block; and the U-nail gasket partially or completely covers the thimble guide grooves.

Further, the lower end surface of the upper comprehensive cover is annular, a convex positioning stage and/or a concave positioning groove is formed along the annular lower end surface of the upper comprehensive cover, the upper end surface of the lower comprehensive cover is annular, a concave positioning groove and/or a convex positioning stage is arranged along the annular upper end surface of the lower comprehensive cover, and the positioning grove and the positioning stage cooperate with each other in a concave-convex manner to position the upper comprehensive cover and the lower comprehensive cover; or the C-type valgus circumcision stapler further comprises a connecting cover arranged between the upper comprehensive cover and the lower comprehensive cover, the upper comprehensive cover is releasably connected to the lower comprehensive cover through the connecting cover, and preferably, a part or all of the U-nail device is placed in the connecting cover; or the C-type valgus circumcision stapler further comprises a connecting cover arranged between the upper comprehensive cover and the lower comprehensive cover, the lower end surface of the upper comprehensive cover is annular, a convex positioning stage and/or a concave positioning groove is formed along the annular lower end surface of the upper comprehensive cover, the upper end surface of the connecting cover is annular, a concave positioning groove and/or a convex positioning stage is arranged along the annular upper end surface of the connecting cover, and the positioning groove and the positioning stage cooperate with each other in a concave-convex manner to position the upper comprehensive cover and the connecting cover.

Further, the upper end surface of the connecting cover is annular, and the convex positioning stage is arranged along the annular upper end surface of the connecting cover, and cooperates with the positioning groove formed on the lower end surface of the upper comprehensive cover for positioning; one or more hooks are arranged at the lower portion of the connecting cover; one or more hooks are arranged at the upper portion of the lower comprehensive cover; and the hooks of the connecting cover and the lower comprehensive cover cooperate with each other for positioning.

Further, the C-type valgus circumcision stapler further comprises a locking ring, wherein an internal thread is arranged on the inner ring surface of the locking ring; an external thread is formed on the outer surface of the lower end of the upper comprehensive cover, and/or is formed on the outer surface of the upper end of the connecting cover, and/or is formed on the outer surface of the upper end of the lower comprehensive cover; and the internal thread and the external thread cooperate with each other to position the upper comprehensive cover, the connecting cover, the lower comprehensive cover and/or the locking ring.

Further, a second through hole is formed in the middle of the upper comprehensive cover, the upper comprehensive cover is provided with an inner cavity for accommodating and/or positioning the prepuce fixing hoop, the prepuce fixing hoop is a ring having a third through hole in the middle, and the third through hole corresponds to the second through hole; and/or, one or more positioning grooves are formed in the inner cavity of the upper comprehensive cover, one or more positioning stages are arranged on the outer surface of the prepuce fixing hoop, and each positioning groove and the corresponding positioning stage cooperate with each other for positioning; and/or, the C-type valgus circumcision stapler further comprises a circumcision knife sleeving the thimble guide block and/or the U-nail top ring, and preferably, the circumcision knife is driven by the U-nail top ring to move; and/or, the C-type valgus circumcision stapler further comprises a blade gasket which is arranged on the lower end surface of the prepuce fixing hoop and which corresponds to the circumcision knife; and/or, a part of the U-nail device is placed in the lower comprehensive cover, and the other part of the U-nail device is placed in the connecting cover; and/or, the C-type valgus circumcision stapler further comprises a connecting block, the upper end of the connecting block being connected to the lower end of the lower comprehensive cover; and/or, the C-type valgus circumcision stapler further comprises a push rod, the upper end of the push rod being inserted into the lower end of the connecting block; and/or, the C-type valgus circumcision stapler further comprises a plug arranged at the lower end of the push rod; and/or, the C-type valgus circumcision stapler further comprises a handle which is drivingly connected to the connecting block and/or push rod, and which is configured to drive the push rod, and/or the connecting block, and/or an internal transmission member of the push rod and/or an internal transmission member of the connecting block so as to drive the U-nail top ring and/or the circumcision knife to move upward; and/or, a ring of a concave/convex structure for being docked with blood vessels is formed on the outer surface of the lower end of the prepuce fixing hoop.

Compared with the prior art, through the structure of the valgus circumcision stapler provided in the present invention, a front prepuce and most of a penis can be accommodated during a surgery, so that the prepuce and the penis are protected from injury or infection. With the structure including the inner ring (the prepuce fixing hoop) and the inner comprehensive cover (U-nail top ring and/or thimble guide block), a portion above a prepuce clamping portion of the circumcision stapler is located in the circumcision stapler. The U-nail grooves are annularly formed in a relatively lower portion inside the inner comprehensive cover (U-nail top ring and/or thimble guide block), so that a U-nail suturing position is located inside the circumcision stapler to avoid hemorrhage caused by instrument failure or misoperation, avoiding a surgical accident arising from infection. The C-type valgus circumcision stapler provided in the present invention has the external circumcision knife, and carries out cutting outside and nailing inside. In case of a redundant prepuce or the like, the pain and risk caused by cutting of overlapped tissues is avoided. Through the blood vessel docking device arranged on the inner ring (prepuce fixing hoop), when the upper cover (upper comprehensive cover) and the lower cover (lower comprehensive cover/connecting cover) cooperate with each other and the inner ring (prepuce fixing hoop) and the inner comprehensive cover (U-nail top ring and/or thimble guide block) cooperate with each other, whether a prepuce blood vessel corresponds to the U-nail can be accurately determined, so that the final positioning of the inner ring (prepuce fixing hoop) and the inner comprehensive cover (U-nail top ring and/or thimble guide block) as well as the upper cover (upper comprehensive cover) and the lower cover (lower comprehensive cover/connecting cover) can be carried out after the blood vessel is positioned accurately, thereby greatly improving the hemostasis effect in the surgery. Preferably, the blood vessel docking grooves can be flexibly arranged to be in one-to-one correspondence with cooperative relationships among the U-nail grooves, the U-nails in the U-nail grooves and the intervals among the U-nail grooves, widths of the U-nail grooves, the U-nails and the intervals among the U-nail grooves, etc., so as to meet requirements of different circumcision devices and surgeries. Thus, the main surface of the U-nail can close the blood vessel, so that the hemostasis effect is excellent during the surgery, and the prepuce necrosis is accelerated after the surgery. More preferably, with the U-nail gasket, when being hammered into the prepuce, the U-nail will not adhere with the prepuce, thereby avoiding the pain in the patient caused by failure of the peeling off of the U-nail later.

BRIEF DESCRIPTION OF THE DRAWINGS

Refer to the C-type valgus circumcision stapler.

SPECIFIC DESCRIPTION OF THE EMBODIMENTS

Refer to the C-type valgus circumcision stapler.

The present invention will be described in detail below with reference to the accompanying drawings. The followings show preferred embodiments in various embodiments of the present invention.

Figure 1:
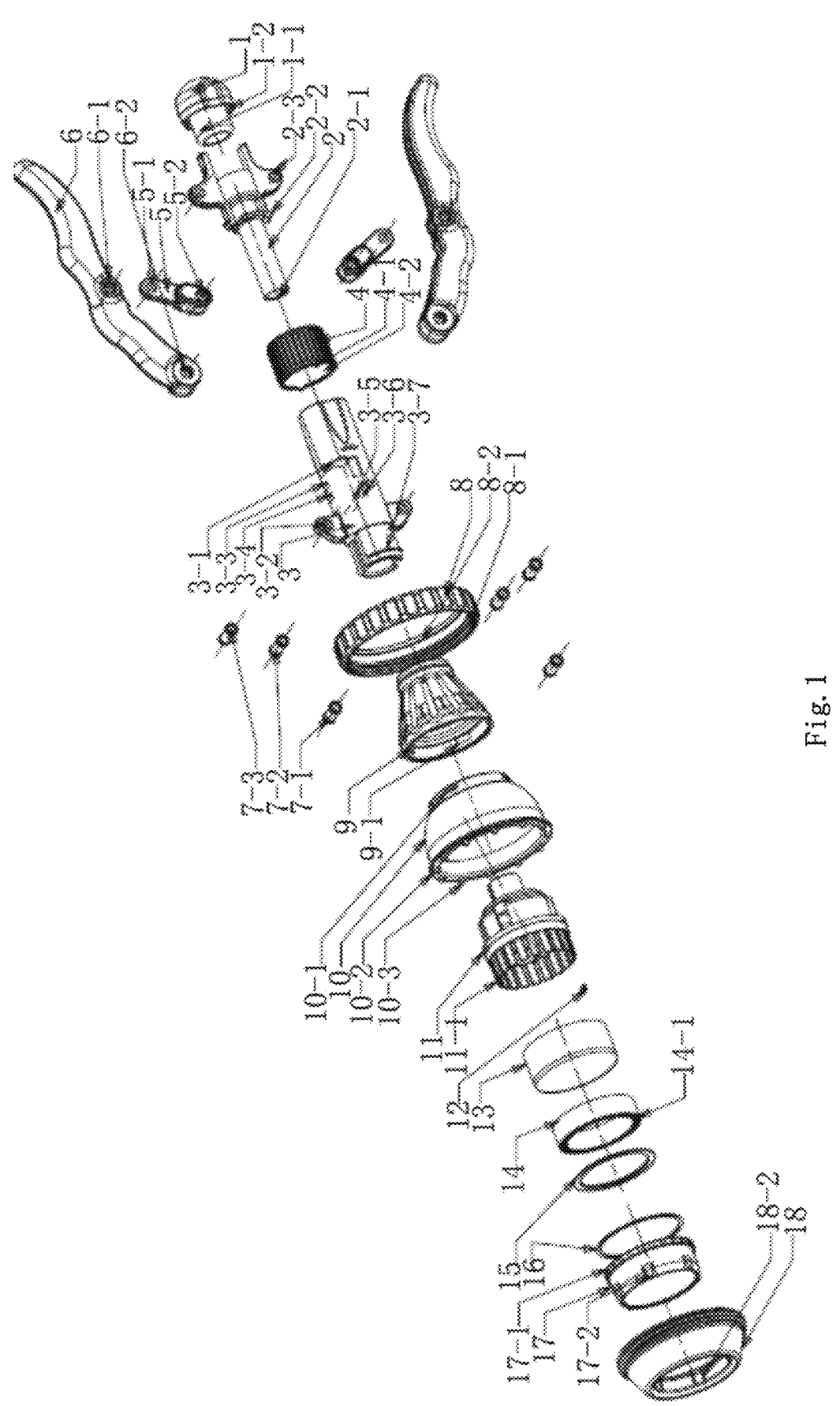
FIG. 1 is an exploded view of a valgus circumcision stapler.
Figure 2:
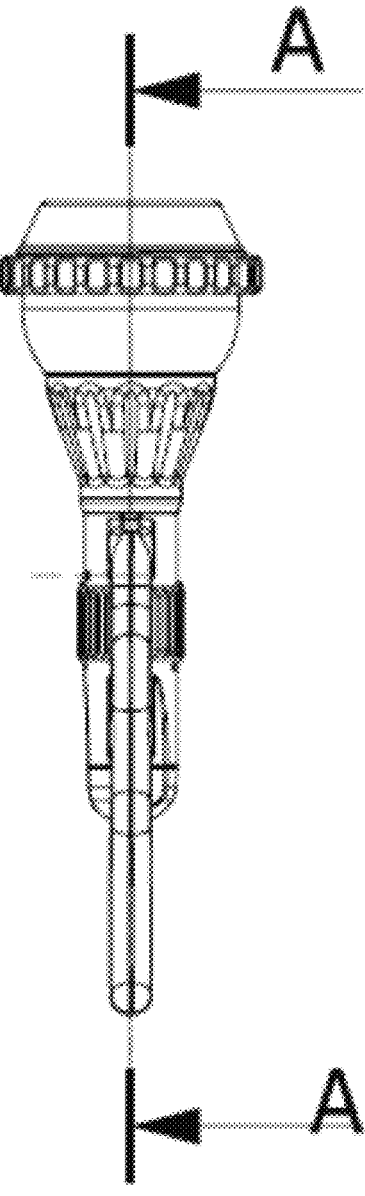
FIG. 2 is a side view of the valgus circumcision stapler.
Figure 3:
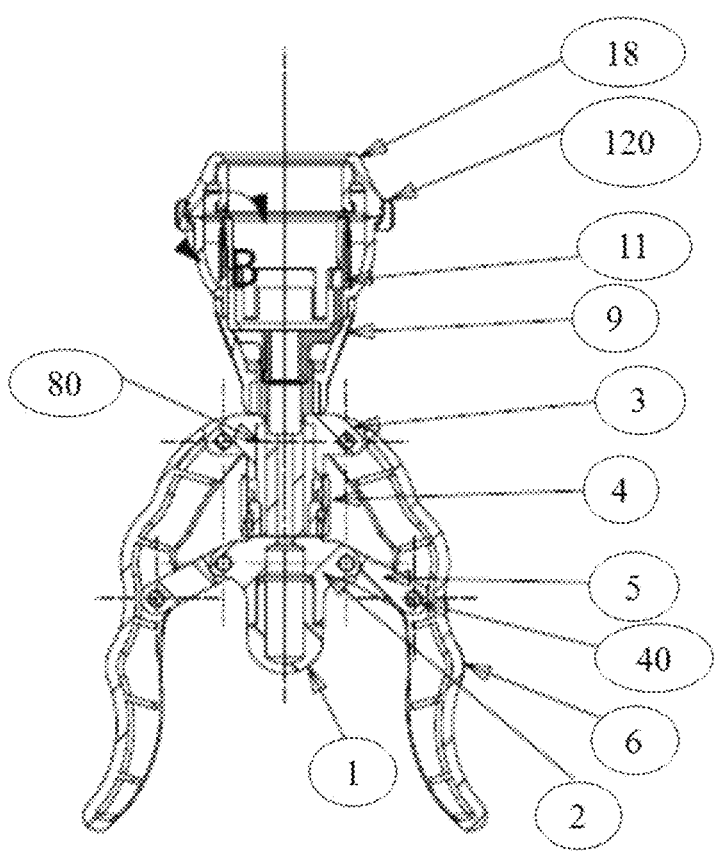
FIG. 3 is a structural view of the valgus circumcision stapler.

FIGS. 1-3 are exploded views of a valgus circumcision stapler. The valgus circumcision stapler includes a plug 1, a circular stage 1-1, a groove 1-2, a push rod 2, a convex stage 2-1, a first hook 2-2, a first pin hole 2-3, a connecting block

3, a guide groove 3-1, a second pin hole 3-2, a first hanging stage 3-3, a second hanging stage 3-4, a closing indicator 3-5, an opening indicator 3-6, a second hook 3-7, an opening knob 4, a pointer 4-1, a middle circular hole 4-2, a guide block 4-3, a small connecting rod 5, a third pin hole 5-1, a fourth pin hole 5-2, a handle 6, a fifth pin hole 6-1, a sixth pin hole 6-2, a first pin 7-1, a second pin 7-2, a third pin 7-3, a locking ring 8, a thread 8-1, a clamping ring 8-2, a lower comprehensive cover 9, a hook 9-1, a connecting cover 10, a hook 10-1, a clamping ring 10-2, a convex positioning stage 10-3, a U-nail top ring 11, a U-nail 12, a circumcision knife 13, a thimble guide block 14, a thimble guide groove 14-1, a U-nail gasket 15, a gasket positioning stage 15-1, a blade gasket 16, a prepuce fixing hoop 17, a blood vessel docking groove 17-1, a positioning stage 17-2, an upper comprehensive cover 18, and a positioning groove 18-2. The valgus circumcision stapler includes the upper comprehensive cover 18, the lower comprehensive cover 9, the prepuce fixing hoop 17 and a U-nail device. The upper comprehensive cover 18 and the lower comprehensive cover 9 are releasably connected in a matching manner. The prepuce fixing hoop 17 is placed in the upper comprehensive cover 18. The U-nail device is placed in the lower comprehensive cover 9. The prepuce fixing hoop 17 is capable of being positioned in the upper comprehensive cover 18 and cooperates with the upper comprehensive cover 18 to clamp a prepuce. The lower end of the prepuce fixing hoop 17 is capable of cooperating with the U-nail device to clamp the prepuce.

The U-nail device comprises the U-nail top ring 11 and the thimble guide block 14. The thimble guide block 14 is configured to accommodate a suturing U-nail 12, to guide the movement of the suturing U-nail 12, to position and guide the thimble of the U-nail top ring 11. The U-nail top ring 11 is configured to cooperate with the thimble guide block 14 to eject the U-nail 12 in the thimble guide block 14. The C-type valgus circumcision stapler further comprises the U-nail gasket 15 which is an annular gasket arranged at the top end of the thimble guide block 14. The U-nail gasket 15 further comprises a gasket positioning stage 15-1 perpendicular to the plane of the U-nail gasket 15. The gasket positioning stage 15-1 is an integral annular protrusion arranged at the inner circumference or the outer circumference or the middle of the plane of the U-nail gasket 15. A first through hole is formed in the middle of the thimble guide block 14. The thimble guide block 14 comprises an annular inner wall, an annular outer wall and a positioning stage accommodating groove. The annular inner wall is configured to cooperate with the annular protrusion arranged at the inner circumference of the plane of the U-nail gasket 15 for positioning. The annular outer wall is configured to cooperate with the annular protrusion arranged at the outer circumference of the plane of the U-nail gasket 15 for positioning. The positioning stage accommodating groove is formed at the top end of the thimble guide block 14, and is configured to accommodate the annular protrusion at the middle of the plane of the U-nail gasket 15. The thimble guide block 14 is provided with a plurality of thimble guide grooves 14-1 annularly formed in the annular thimble guide block 14. The U-nail gasket 15 completely covers the thimble guide grooves 14-1.

The C-type valgus circumcision stapler further comprises the connecting cover 10 arranged between the upper comprehensive cover 18 and the lower comprehensive cover 9. The upper comprehensive cover 18 is releasably connected to the lower comprehensive cover 9 in a matching manner through the connecting cover 10. The lower end surface of the upper comprehensive cover 18 is annular. A concave positioning groove is formed along the annular lower end surface of the upper comprehensive cover 18. The upper end surface of the connecting cover 10 is annular. A convex positioning stage 10-3 is arranged along the annular upper end surface of the connecting cover 10. The positioning groove and the convex positioning stage 10-3 cooperate with each other in a concave-convex manner to position the upper comprehensive cover 18 and the connecting cover 10. The upper end surface of the connecting cover 10 is annular. The convex positioning stage 10-3 is arranged along the annular upper end surface of the connecting cover 10, and cooperates with the positioning groove formed on the lower end surface of the upper comprehensive cover 18 for positioning. A plurality of hooks 10-1 is arranged at the lower portion of the connecting cover 10. A plurality of hooks 9-1 is arranged at the upper portion of the lower comprehensive cover 9. The hooks of the connecting cover 10 and the lower comprehensive cover 9 cooperate with each other for positioning.

The C-type valgus circumcision stapler further comprises the locking ring 8. The internal thread 8-1 and/or the clamping ring 8-2 are/is arranged on the inner ring surface of the locking ring 8. The external thread is arranged on the outer surface of the lower end of the upper comprehensive cover 18. The external thread or the clamping ring 10-2 is arranged on the outer surface of the upper end of the connecting cover 10. The internal thread 8-1 and the external thread cooperate with each other, and/or the clamping rings 8-2/10-2 cooperate with each other to position the upper comprehensive cover 18, the connecting cover 10, the lower comprehensive cover 9 and the locking ring 8.

Figure 9:
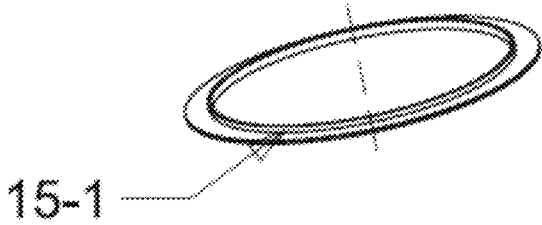
FIG. 9 is an enlarged view of a U-nail gasket.
Figure 10:
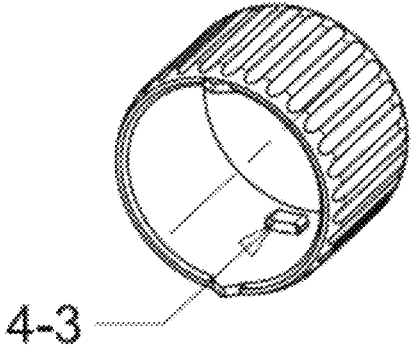
FIG. 10 is an enlarged view of an opening knob.

A second through hole is formed in the middle of the upper comprehensive cover 18. The upper comprehensive cover 18 is provided with an inner cavity for accommodating and positioning the prepuce fixing hoop 17. The prepuce fixing hoop 17 is a ring having a third through hole in the middle, and the third through hole corresponds to the second through hole. A plurality of positioning grooves is formed in the inner cavity of the upper comprehensive cover 18. A plurality of positioning stages 17-2 is arranged on the outer surface of the prepuce fixing hoop 17, and each positioning groove 18-2 and the corresponding positioning stage 17-2 cooperate with each other for positioning. The C-type valgus circumcision stapler further comprises the circumcision knife 13 sleeving the thimble guide block 14 and the U-nail top ring 11, and the circumcision knife 13 is driven by the U-nail top ring 11 to move. The C-type valgus circumcision stapler further comprises the blade gasket 16 which is arranged on the lower end surface of the prepuce fixing hoop 17 and which corresponds to the circumcision knife 13. A part of the U-nail device is placed in the lower comprehensive cover 9, and the other part of the U-nail device is placed in the connecting cover 10. The C-type valgus circumcision stapler further comprises the connecting block 3, the upper end of the connecting block 3 being connected to the lower end of the lower comprehensive cover 9. The C-type valgus circumcision stapler further comprises a push rod, the upper end of the push rod being inserted into the lower end of the connecting block 3. The C-type valgus circumcision stapler further comprises a plug 1 arranged at the lower end of the push rod. The C-type valgus circumcision stapler further comprises a handle 6 which is drivingly connected to the connecting block 3 and the push rod 2, and which is configured to drive the push rod 2 and an internal transmission member of the connecting block so as to drive the U-nail top ring 11 and the circumcision knife 13 to move upward. A ring of a blood vessel docking groove 17-1 for being docked with blood vessels is formed on the outer surface of the lower end of the prepuce fixing hoop. The C-type valgus circumcision stapler further comprises the opening knob 4 which sleeves the connecting block 3 and which is configured to lock or unlock the handle and/or a component driven by the handle. FIGS. 9 and 10 are enlarged views of the U-nail gasket and the opening knob, respectively. The pointer 4-1 is arranged at the upper end of the opening knob 4. The circular hole 4-2 is formed in the middle of the opening knob 4. The inner wall of the opening knob 4 is provided with the guide block 4-3 which cooperates with the guide groove 3-1 formed on the connecting block 3 to lock or unlock the handle 6 or other driving members. The gasket positioning stage 15-1 is arranged at one side of the U-nail gasket 11 to position the U-nail gasket on the thimble guide block 14.

Figure 4:
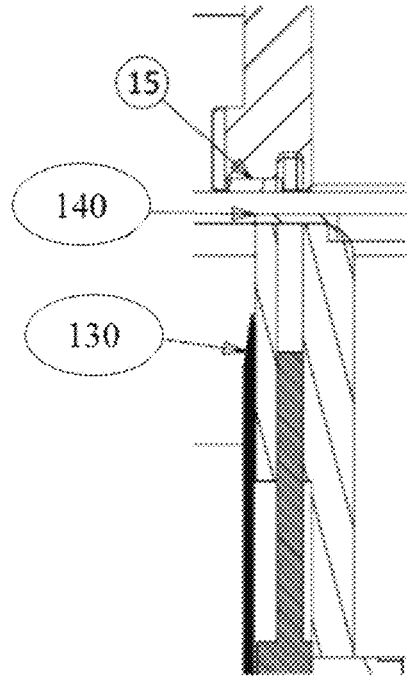
FIG. 4 is an enlarged view of portion B shown in FIG. 3.
Figure 5:
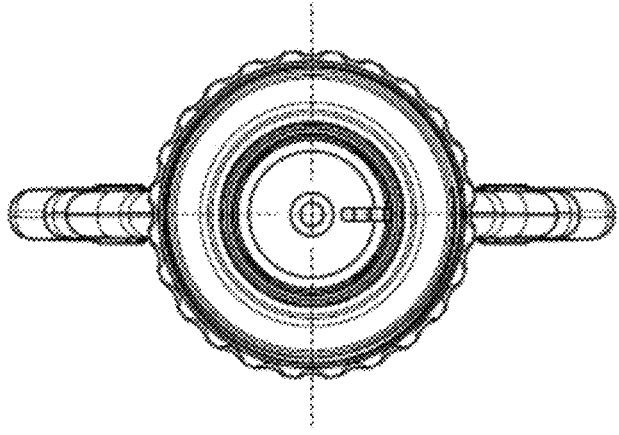
FIG. 5 is a top view of the valgus circumcision stapler.
Figure 6:
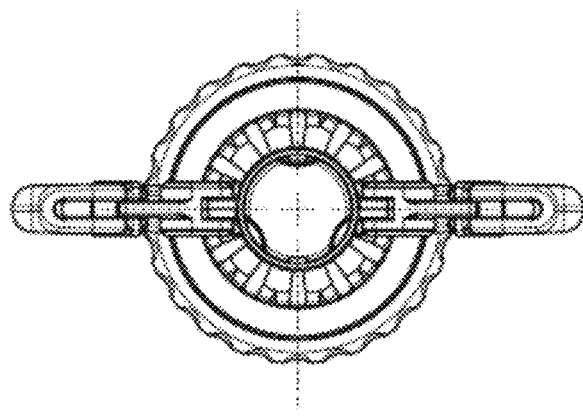
FIG. 6 is a bottom view of the valgus circumcision stapler.
Figure 7:
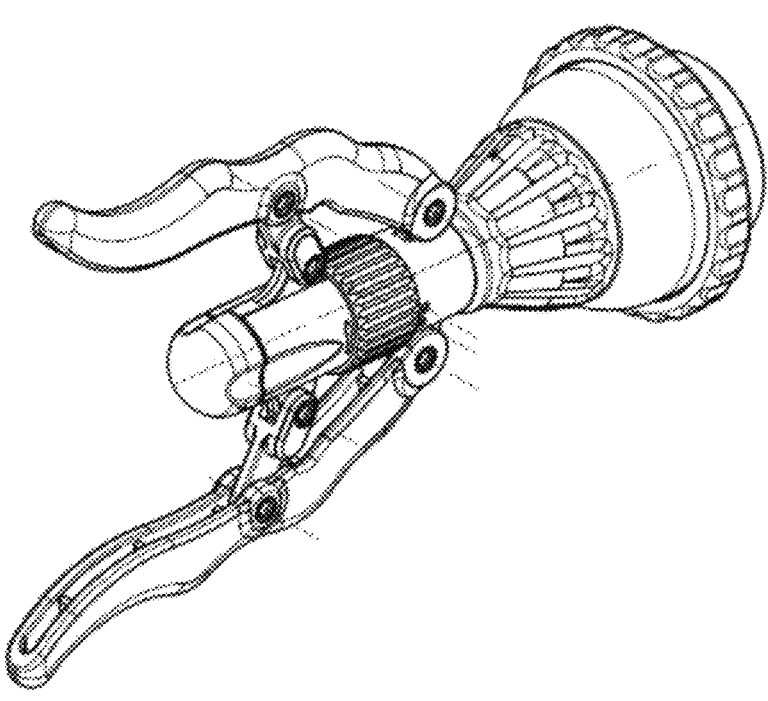
FIG. 7 is a perspective view of the valgus circumcision stapler.
Figure 8:
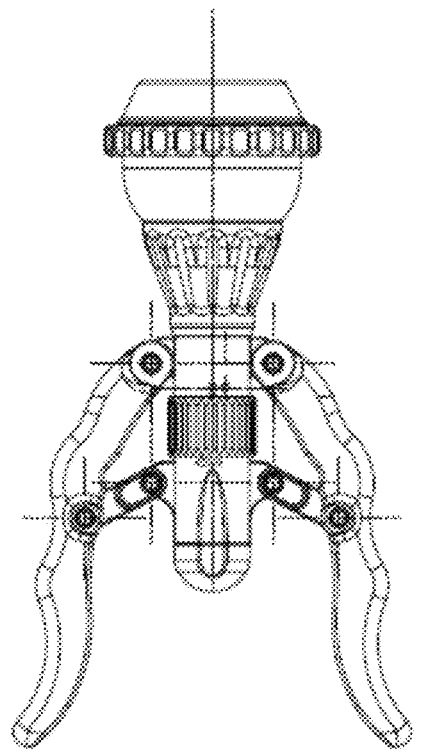
FIG. 8 is a front view of the valgus circumcision stapler.

FIG. 8 is a front view of the valgus circumcision stapler. In order to describe the specific structure of the valgus circumcision stapler more clearly according to the drawings, FIGS. 2 and 5-7 are views of the valgus circumcision stapler from all visual angles. Referring to FIGS. 3 and 4, in the preferred embodiment, the valgus circumcision stapler includes a handle 6, a plug 1, a small connecting rod 5, a pin 40, a push rod 2, a connecting block 3, an opening knob 4, a spring 80, a lower comprehensive cover 9, a U-nail top ring 11, an upper comprehensive cover 18, a threaded locking ring 120, a circumcision knife 13, a U-nail washer 140 and a circumcision knife gasket 150. The handle 6 is drivingly connected to the push rod 2 and the connecting block 3 through the small connecting rod 5 and the pin 40. The opening knob 4 sleeves the connecting block 3. The plug 1 is arranged at the lower end of the push rod 2. The upper comprehensive cover 18 and the lower comprehensive cover 9 are directly connected or connected through a connecting cover. The spring 80 is arranged in the inner cavity of the connecting block 3. A part or all of the U-nail top ring 11 is arranged in the lower comprehensive cover 9; or a part or all of the U-nail top ring 11 is arranged in the connecting cover; or a part of the U-nail top ring 11 is arranged in the lower comprehensive cover 9, and the other part of the U-nail top ring 11 is arranged in the connecting cover. The threaded locking ring 120 locks the peripheries of the upper comprehensive cover 18 and/or the lower comprehensive cover 9 and/or the connecting cover. The circumcision knife 13 is arranged at the periphery of the U-nail top ring 11 and the guide block. The U-nail washer 140 is fixed at the top end of a U-nail groove, so that the U-nail preferably penetrates through the U-nail washer 140 to avoid contact between one or more surfaces of the U-nail and a prepuce tissue when the U-nail is hammered into the prepuce. The principles of other related driving components, actuating components and circumcision components are the same as those in the previous embodiment, and are not repeated herein.

The above description of the present invention has been given by way of example with reference to the accompanying drawings. It is obvious that the specific implementation of the present invention is not limited to the above modes, and various improvements made using the method concepts and technical solutions of the present invention or directly applied to other occasions, are within the scope of the present invention.

The invention claimed is:

1. A C-type valgus circumcision stapler, comprising: an upper comprehensive cover, a lower comprehensive cover, a prepuce fixing hoop and a U-nail device, wherein the upper comprehensive cover and the lower compre-
hensive cover are releasably connected in a matching
manner;

a part or all of the prepuce fixing hoop is placed in the
upper comprehensive cover;

a part or all of the U-nail device is placed in the lower
comprehensive cover;

the prepuce fixing hoop cooperates with the upper com-
prehensive cover to clamp a prepuce, and/or a lower
end of the prepuce fixing hoop is capable of cooperat-
ing with the U-nail device to clamp the prepuce;

wherein the U-nail device comprises a U-nail top ring and
a thimble guide block;

a ring of a blood vessel docking groove for being docked
with blood vessels is formed on an outer surface of a
lower end of the prepuce fixing hoop; and the C-type valgus circumcision stapler further comprises
a circumcision knife sleeving the thimble guide block
and/or the U-nail top ring.

2. The C-type valgus circumcision stapler of claim 1,
wherein the thimble guide block is configured to accommo-
date a suturing U-nail and/or to guide the movement of the
suturing U-nail and/or to position and/or guide a thimble of
the U-nail top ring; and the U-nail top ring is configured to
cooperate with the thimble guide block to eject the U-nail in
the thimble guide block.

3. The C-type valgus circumcision stapler of claim 2,
further comprising a U-nail gasket which is an annular
gasket arranged at the top end of the thimble guide block.

4. The C-type valgus circumcision stapler of claim 3,
wherein the U-nail gasket further comprises a gasket posi-
tioning stage perpendicular to and/or at an angle to the plane
of the U-nail gasket; and the gasket positioning stage is one
or more protrusions and/or an integral annular protrusion
arranged at the inner circumference and/or the outer circum-
ference and/or the middle of the plane of the U-nail gasket.

5. The C-type valgus circumcision stapler of claim 4,
wherein a first through hole is formed in the middle of the
thimble guide block; the thimble guide block comprises an
annular inner wall and/or an annular outer wall and/or a
positioning stage accommodating groove; the annular inner
wall is configured to cooperate with the one or more
protrusions and/or integral annular protrusion arranged at
the inner circumference of the plane of the U-nail gasket for
positioning; and/or, the annular outer wall is configured to
cooperate with the one or more protrusions and/or integral
annular protrusion arranged at the outer circumference of the
plane of the U-nail gasket for positioning; and/or, the
positioning stage accommodating groove is formed at the
top end of the thimble guide block, and is configured to
accommodate the one or more protrusions and/or integral
annular protrusion at the middle of the plane of the U-nail
gasket.

6. The C-type valgus circumcision stapler of claim 3,
wherein the thimble guide block is provided with a plurality
of thimble guide grooves annularly formed in the annular
thimble guide block; and the U-nail gasket partially or
completely covers the thimble guide grooves.

7. The C-type valgus circumcision stapler of claim 1,
wherein the lower end surface of the upper comprehensive
cover is annular, a convex positioning stage and/or a con-
cave positioning groove is formed along the annular lower
end surface of the upper comprehensive cover, the upper end
surface of the lower comprehensive cover is annular, a
concave positioning groove and/or a convex positioning
stage is arranged along the annular upper end surface of the
lower comprehensive cover, and the positioning grove and the positioning stage cooperate with each other to position
the upper comprehensive cover and the lower comprehen-
sive cover;

or, the C-type valgus circumcision stapler further comprises
a connecting cover arranged between the upper com-
prehensive cover and the lower comprehensive cover,
the upper comprehensive cover is releasably connected
to the connecting cover, the connecting cover is releas-
ably connected to the lower comprehensive cover, and
preferably, a part of the U-nail device is placed in the
connecting cover;

or, the C-type valgus circumcision stapler further comprises
a connecting cover arranged between the upper com-
prehensive cover and the lower comprehensive cover,
the lower end surface of the upper comprehensive
cover is annular, a convex positioning stage and/or a
concave positioning groove is formed along the annular
lower end surface of the upper comprehensive cover,
the upper end surface of the connecting cover is annu-
lar, a concave positioning groove and/or a convex
positioning stage is arranged along the annular upper
end surface of the connecting cover, and the positioning
groove and the positioning stage cooperate with each
other in a concave-convex manner to position the upper
comprehensive cover and the connecting cover.

8. The C-type valgus circumcision stapler of claim 7,
wherein the upper end surface of the connecting cover is
annular, and the convex positioning stage is arranged along
the annular upper end surface of the connecting cover, and
cooperates with the positioning groove formed on the lower
end surface of the upper comprehensive cover for position-
ing; one or more hooks are arranged at the lower portion of
the connecting cover; one or more hooks are arranged at the
upper portion of the lower comprehensive cover; and the
hooks of the connecting cover and the lower comprehensive
cover cooperate with each other for positioning.

9. The C-type valgus circumcision stapler of claim 1,
further comprising a locking ring, wherein an internal thread
and/or a first clamping ring is arranged on the surface of an
inner ring of the locking ring; an external thread is formed
on the outer surface of the lower end of the upper compre-
hensive cover, and/or the external thread or a second clamp-
ing ring is arranged on the outer surface of the upper end of
the connecting cover, and/or the external thread is formed on
the outer surface of the upper end of the lower comprehen-
sive cover; and the internal thread and the external thread
cooperate with each other, and/or the first and second
clamping rings cooperate with each other to position the
upper comprehensive cover, the connecting cover, the lower
comprehensive cover and/or the locking ring.

10. The C-type valgus circumcision stapler of claim 1,
wherein a second through hole is formed in the middle of the upper
comprehensive cover, the upper comprehensive cover
is provided with an inner cavity for accommodating
and/or positioning the prepuce fixing hoop, the prepuce
fixing hoop is a ring having a third through hole in the
middle, and the third through hole corresponds to the
second through hole;

and/or, one or more positioning grooves are formed in an inner
cavity of the upper comprehensive cover, one or more
positioning stages are arranged on the outer surface of the prepuce fixing hoop, and each positioning groove and the corresponding positioning stage cooperate with each other for positioning;

and/or, the circumcision knife is driven by the U-nail top ring to move;

and/or, the C-type valgus circumcision stapler further comprises a blade gasket which is arranged on the lower end surface of the prepuce fixing hoop and which corresponds to the circumcision knife;

and/or, a part of the U-nail device is placed in the lower comprehensive cover, and the other part of the U-nail device is placed in a connecting cover;

and/or, the C-type valgus circumcision stapler further comprises a connecting block, the upper end of the connecting block being connected to the lower end of the lower comprehensive cover;

and/or, the C-type valgus circumcision stapler further comprises a push rod, the upper end of the push rod being inserted into the lower end of the connecting block;

and/or, the C-type valgus circumcision stapler further comprises a plug arranged at the lower end of the pushing rod;

and/or, the C-type valgus circumcision stapler further comprises a handle which is drivingly connected to the connecting block and/or push rod, and which is configured to drive the push rod, and/or the connecting block, and/or an internal transmission member of the push rod and/or an internal transmission member of the connecting block so as to drive the U-nail top ring and/or the circumcision knife to move upward;

and/or, the C-type valgus circumcision stapler further comprises an opening knob which sleeves the connecting block, and which is configured to lock or unlock the handle and/or a component driven by the handle.

* * * * *